United States Patent [19]

Shah

[11] Patent Number: 5,263,987

[45] Date of Patent: Nov. 23, 1993

[54] METHOD AND APPARATUS FOR ARTHROSCOPICALLY REPLACING A BONE JOINT

[76] Inventor: Mrugesh K. Shah, 4314 Monte Video Cir., Pasadena, Tex. 77504

[21] Appl. No.: 705,766

[22] Filed: May 28, 1991

Related U.S. Application Data

[63] Continuation-in-part of Ser. No. 398,678, Aug. 25, 1989, abandoned.

[51] Int. Cl.[5] .............................................. A61F 2/30
[52] U.S. Cl. ........................................ 623/18; 623/20; 606/88; 606/86
[58] Field of Search ................................ 606/86-89, 606/99; 623/18-23

[56] References Cited

U.S. PATENT DOCUMENTS

| | | | |
|---|---|---|---|
| 3,774,244 | 11/1973 | Walker | 623/20 |
| 4,156,296 | 5/1979 | Johnson et al. | 3/1.91 |
| 4,224,699 | 9/1980 | Weber | 3/1.913 |
| 4,274,164 | 6/1981 | Rehder et al. | 3/1.913 |
| 4,642,122 | 2/1987 | Steffee | 623/21 |
| 4,713,077 | 12/1987 | Small | 606/80 X |
| 4,719,908 | 1/1988 | Averill et al. | 606/80 |
| 4,808,185 | 2/1989 | Penenberg et al. | 623/18 X |

FOREIGN PATENT DOCUMENTS

| | | | |
|---|---|---|---|
| 1964781 | 12/1969 | Fed. Rep. of Germany | 623/20 |
| 1902700 | 8/1970 | Fed. Rep. of Germany | 623/18 |
| 2905592 | 8/1979 | Fed. Rep. of Germany | 623/20 |
| 2933141 | 4/1980 | Fed. Rep. of Germany | 623/18 |
| 2465470 | 4/1981 | France | 623/18 |
| 2550936 | 3/1985 | France | 623/18 |

OTHER PUBLICATIONS

Walker, Peter S., PhD., Requirements for Successful Total Knee Replacements, Jan., 1989, Orthopedic Clinics of North America.

Black, Jonathan, PhD., Requirements for Successful Total Knee Replacement, Jan., 1989, Orthopedic Clinics of North America.

*Primary Examiner*—Robert A. Hafer
*Assistant Examiner*—David J. Kenealy
*Attorney, Agent, or Firm*—Ben D. Tobor

[57] ABSTRACT

A method and apparatus for arthroscopically replacing a joint between two bones utilizes a plurality of joint surface members which are attached to a prepared surface arthroscopically formed on the end of a bone, and the joint surface members are inserted through an arthroscopic portal adjacent to the joint to be repaired.

33 Claims, 7 Drawing Sheets

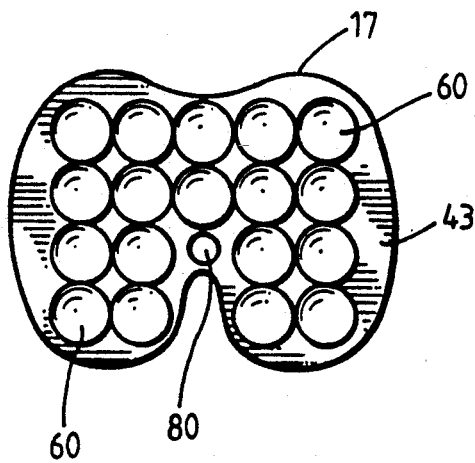
FIG.4
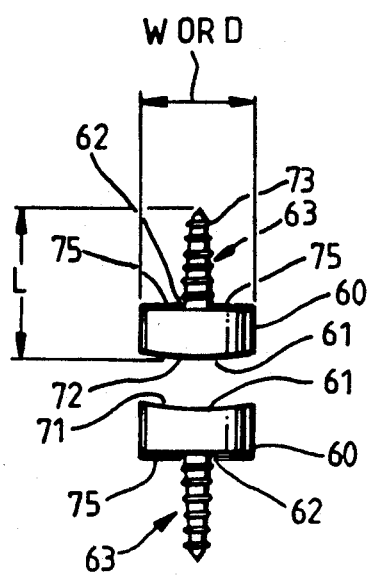
FIG.5
FIG.6
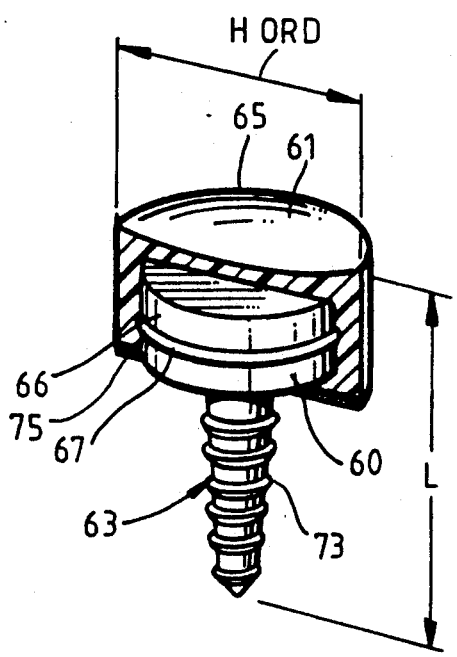
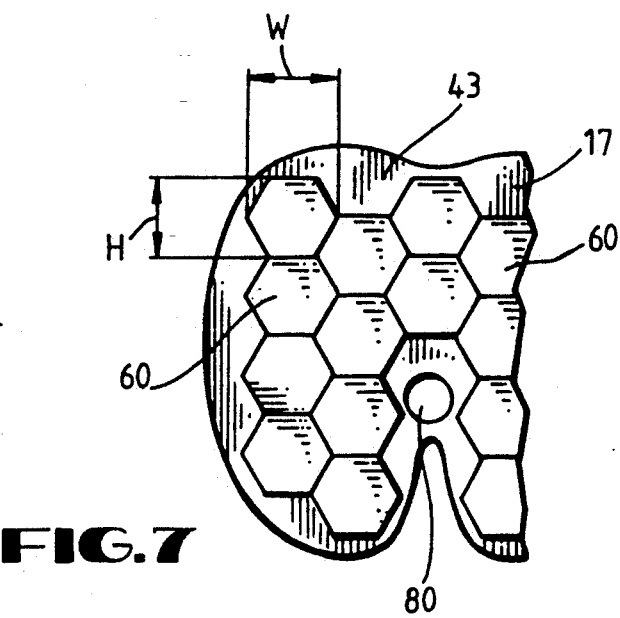
FIG.7

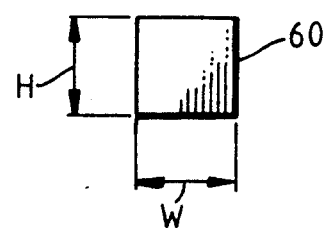
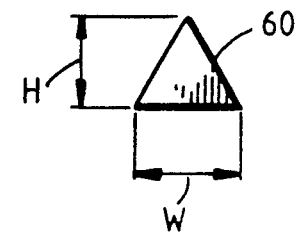
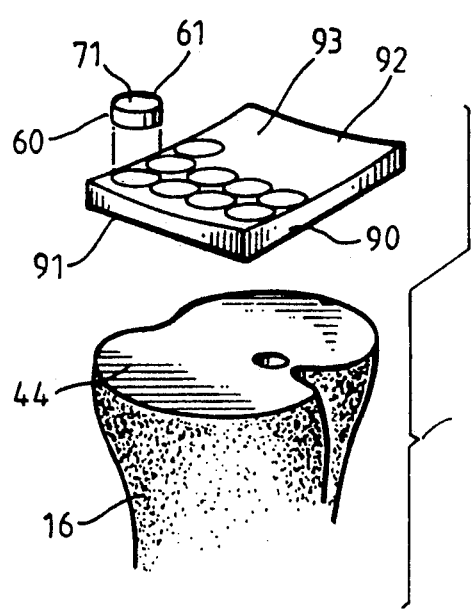
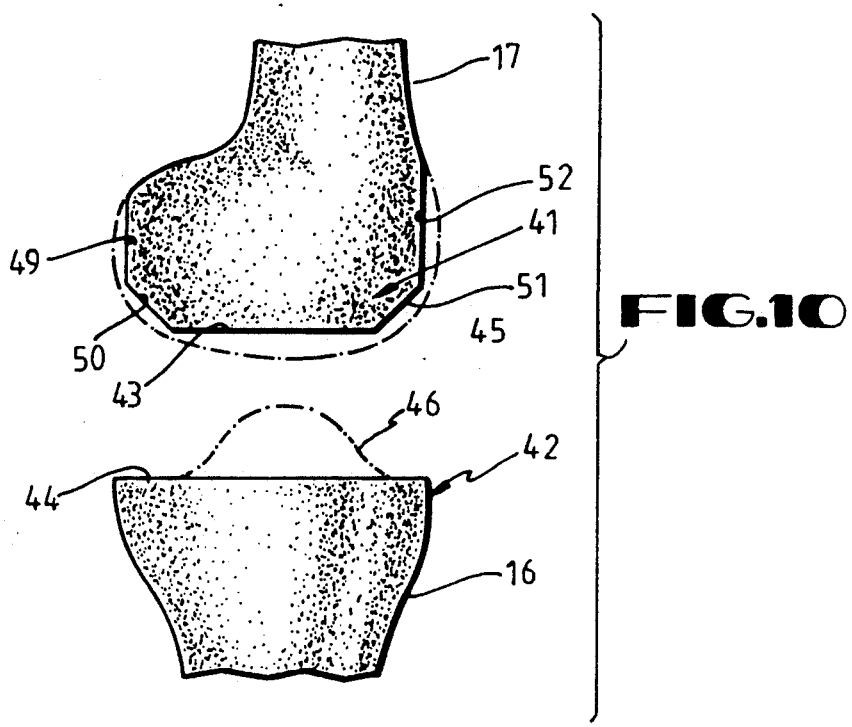

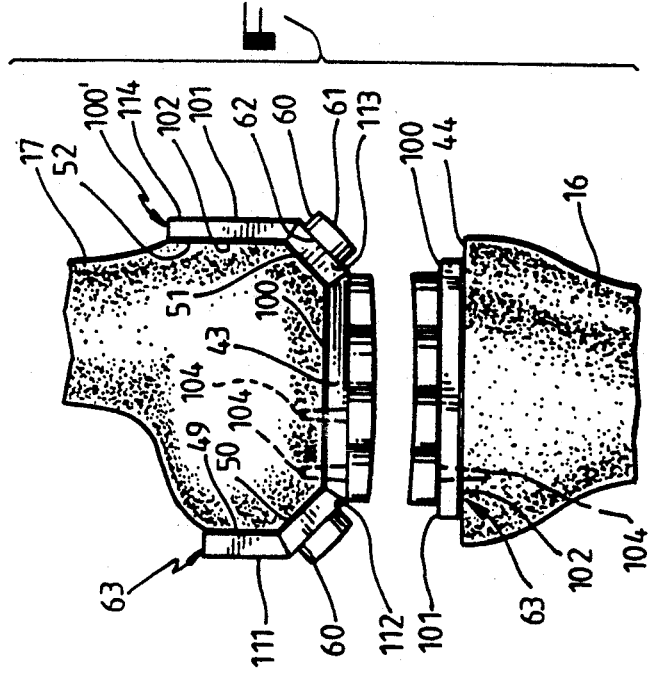
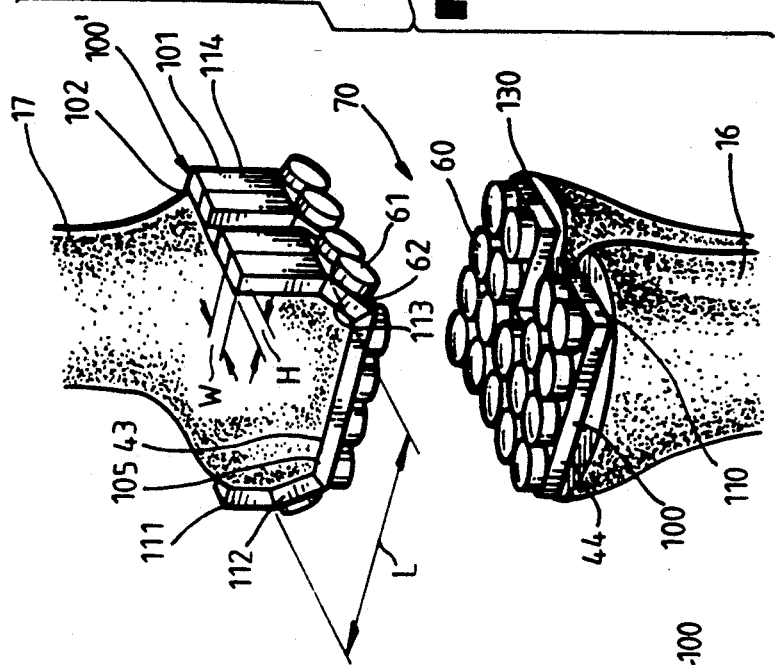
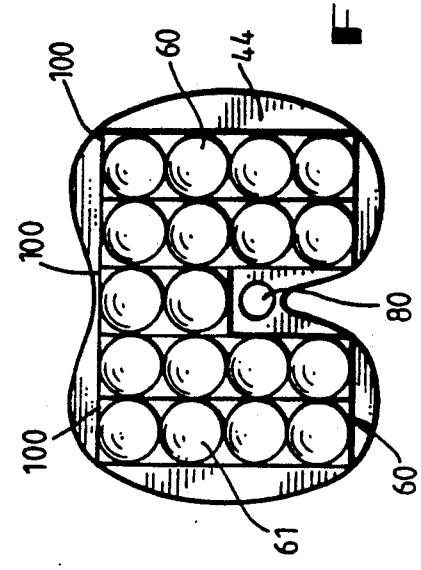

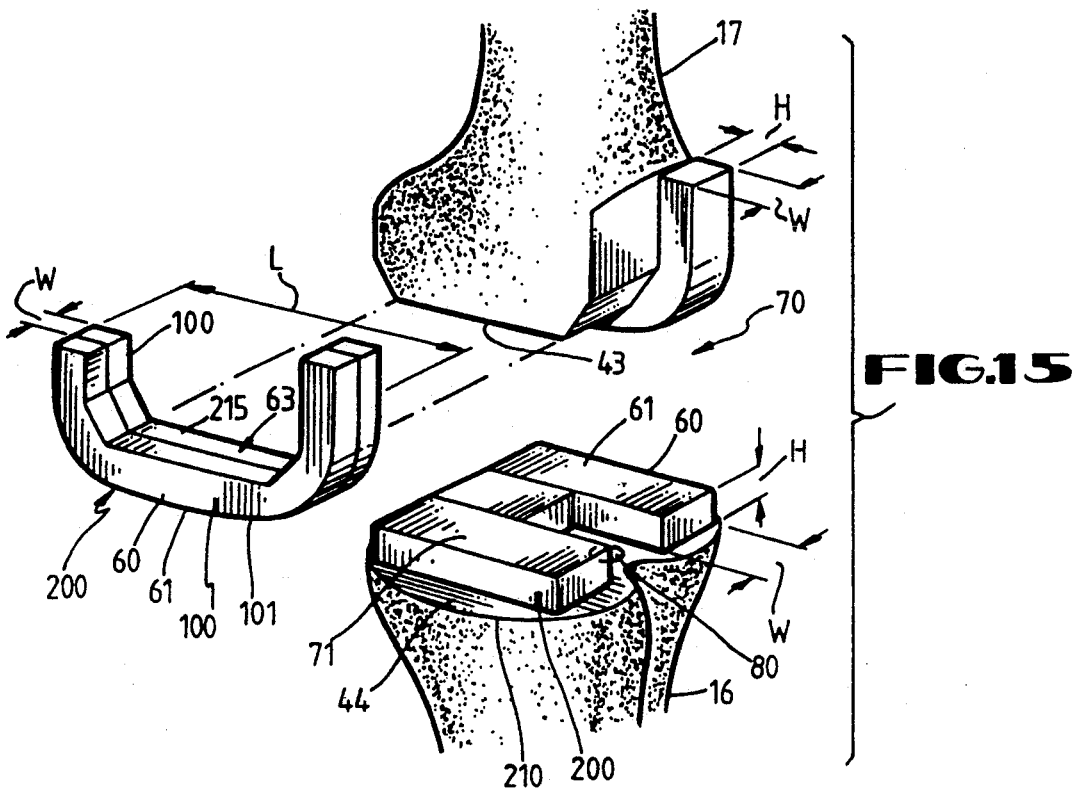
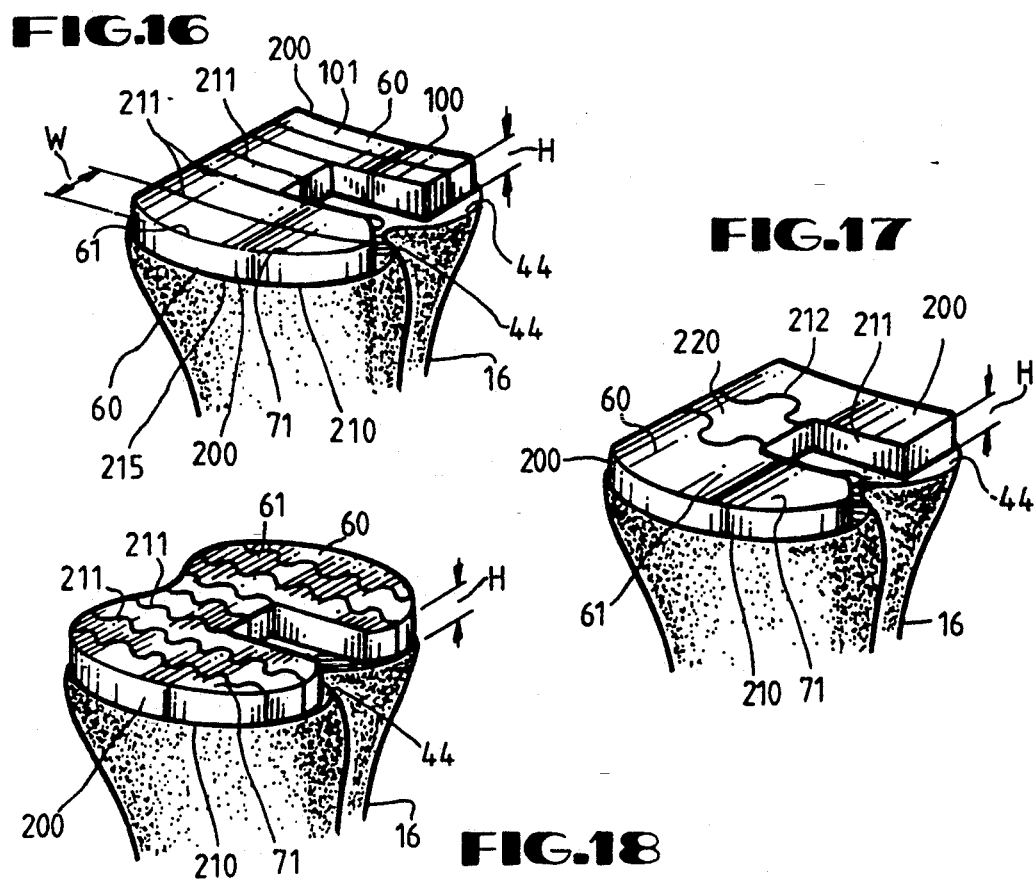

METHOD AND APPARATUS FOR ARTHROSCOPICALLY REPLACING A BONE JOINT

RELATED APPLICATION

This application is a continuation-in-part application of U.S. patent application Ser. No. 07/398,678, filed Aug. 25, 1989 now abandoned.

FIELD OF THE INVENTION

The present invention relates to a method of providing a low friction bone joint replacement by arthroscopic surgery and an apparatus for arthroscopically repairing damaged or diseased joints.

BACKGROUND OF THE INVENTION

It has been known for several years that prosthetic devices can be used for joints to replace defective natural joints. In the patent issued to Johnson and Vegell on May 29, 1979, U.S. Pat. No. 4,156,296, there is described an endoprosthetic device for replacement of the joint in fingers and toes. This device requires removal of part of the bone and the insertion of a device to replace the joint.

The patent issued to Weber on Sept. 30, 1980, U.S. Pat. No. 4,224,699, describes a cap-shaped endoprosthesis and anchoring pin for the replacement of the femoral head.

In the patent issued to Rehder and Rusdea on Jun. 23, 1981, U.S. Pat. No. 4,274,164, there is described an endoprosthesis for replacement of a hip joint including a cap shaped femur head shell device. This device includes a convex surface used for insertion into the hip joint to form a complete replacement of the hip joint.

In a patent issued to Steffee on Feb. 10, 1987, U.S. Pat. No. 4,642,122, there is described a device for an implantable joint replacing a human toe joint.

All of the foregoing patents describe methods and apparatus for replacement of damaged or diseased bone joints with a prosthesis. The major disadvantage associated with these methods of replacing bone joints is that major surgery is required. The bone joint replacement requires a large incision to expose and partially amputate the bone ends so that the joint can be capped. These procedures usually require major surgery performed in a hospital and may require blood transfusions. Recovery after surgery takes weeks and typically requires post operative therapy.

In contrast to these prior art methods and apparatus, the present invention is directed to a method and apparatus for providing low friction bone joint replacement through arthroscopic surgery. A major advantage of the present invention is that the surgical procedure required is considered minor when compared with the prior art methods and apparatus, in that no large incisions are necessary. Additionally, no blood transfusion is typically required. Furthermore, because the procedure is less traumatic, the recovery time should be shorter; and it is believed that the procedure may be performed on an out-patient basis.

SUMMARY OF THE INVENTION

In accordance with the invention, the foregoing advantages have been achieved through the present apparatus for arthroscopically replacing a joint between two bones, each bone having at least one planar surface formed thereon, at least one of the planar surfaces of each bone being disposed opposite each other in a spaced relationship. The present invention includes: a plurality of joint surface members, each joint surface member including an upper bearing surface formed of a bio-compatible, low friction material, and a lower surface; means for attaching the plurality of joint surface members to a prepared bone surface, the attachment means being associated with the lower surface of each joint surface member; each of the joint surface members having three external dimensions including height, width and length, and at least two of the external dimensions of each joint surface member are equal to, or less than, one centimeter, whereby the joint surface members may be passed through an arthroscopic portal adjacent to the joint and a portion of the plurality of the joint surface members may be attached to one prepared bone surface and the remaining portion of the plurality of joint surface members may be attached to the other prepared bone surface to form a replacement joint between the two bones. A feature of the invention is that the attachment means may be either: a screw, pin, nail, or staple member associated with the lower surface of the joint surface members; a bio-compatible glue or bone cement; or may include a porous coating into which the bone may grow.

Another feature of the present invention is that the attachment means may include a plurality of scaffold members upon which are disposed a plurality of joint surface members; the scaffold members having an upper and a lower surface, the lower surface of each joint surface member being disposed upon an upper surface of one of the scaffold members, and the lower surface of each scaffold member may be attached to a prepared bone surface.

Another feature of the present invention is that one of the bones may be a femur having a plurality of prepared planar bone surfaces formed thereon, and the scaffold members which are attached to the planar surfaces of the femur have a J,C, or U-shaped configuration which conforms to the shape of the planar surfaces on the femur. A further feature of the present invention is that the joint surface members may be the scaffold members, and the upper bearing surface of each joint surface may be formed as an integral part of the upper surface of each scaffold member.

An additional feature of the present invention is that the cross-sectional configuration of some of the joint surface members may be circular, triangular, rectangular, or hexagonal. A further feature of the present invention is that the upper bearing surfaces of the joint surface members attached to one bone may have a concave configuration, and the upper bearing surfaces of the joint surface members attached to the other bone may have a convex figuration, whereby opposing upper bearing surfaces are matingly received within one another. Alternatively, the upper bearing surfaces of each joint surface member may be planar or convex.

In accordance with another aspect of the invention, the foregoing advantages have also been achieved through the present method for arthroscopically replacing a joint between two bones. The present invention includes the steps of: forming a plurality of arthroscopic portals adjacent to the joint; inserting an arthroscope through one of the arthroscopic portals; arthroscopically preparing at least one surface on each bone with at least one of the prepared surfaces of each bone being disposed opposite each other in a spaced relationship;

inserting a plurality of joint surface members through at least some of the arthroscopic portals, each joint surface member including an upper bearing surface formed of a bio-compatible, low friction material, and a lower surface; attaching a plurality of joint surface members to the prepared bone surfaces to cover a substantial portion of each prepared bone surface, whereby a replacement joint between the two bones is formed by the upper bearing support surfaces of the joint surface members which upper bearing surfaces abut oppositely disposed upper bearing surfaces as one bone moves with respect to the other bone.

A further feature of the present invention may include the steps of: inserting a plurality of scaffold members through some of the arthroscopic portals; attaching the scaffold members to the prepared bone surfaces, and attaching the joint surface members to the scaffold members. A further feature of the present invention is the step of forming the upper bearing surfaces as an integral part of each scaffold member.

The method and apparatus for arthroscopically replacing a bone joint of the present invention, when compared with previously proposed prior art methods and apparatus, have the advantages of: not requiring a major surgical procedure which includes large incisions to expose the bone ends of the joint to be repaired; does not require blood transfusions; may be performed on a out-patient basis; and has a shorter recovery time.

BRIEF DESCRIPTION OF THE DRAWINGS

In the drawings:

FIG. 4 is a partial cross-sectional view of a femur in accordance with the present invention taken along the lines of 4—4 of FIG. 3;

FIG. 5 is a side view of one embodiment of a joint surface member in accordance with the present invention;

FIG. 6 is a partial cross-sectional view of another embodiment of a joint surface member in accordance with the present invention;

FIG. 7 is a partial cross-sectional view of a femur, similar to that of FIG. 4, illustrating another embodiment of a plurality of joint surface members in accordance with the present invention.

FIGS. 8A and 8B, are top views of other embodiments of joint surface members in accordance with the present invention;

FIG. 9 is an exploded prospective view of a tibia, illustrating one example of how to manufacture joint surface members in accordance with the present invention;

FIG. 10 is a side view of a femur and a tibia, illustrating another embodiment of preparing a femur and a tibia for use with the present invention;

FIG. 11 is a side view of the femur and tibia of FIG. 10, provided with the apparatus of the present invention;

FIG. 12 is a top view of a femur and a tibia provided with a plurality of scaffold members in accordance with the present invention;

FIG. 13 is an exploded perspective view of the tibia and femur of FIG. 11;

FIG. 15 is an exploded, perspective view of a femur and tibia provided with another embodiment of the apparatus of the present invention;

FIGS. 15-18 are perspective views of a tibia, each provided with a different embodiment of the apparatus of the present invention;

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1A:
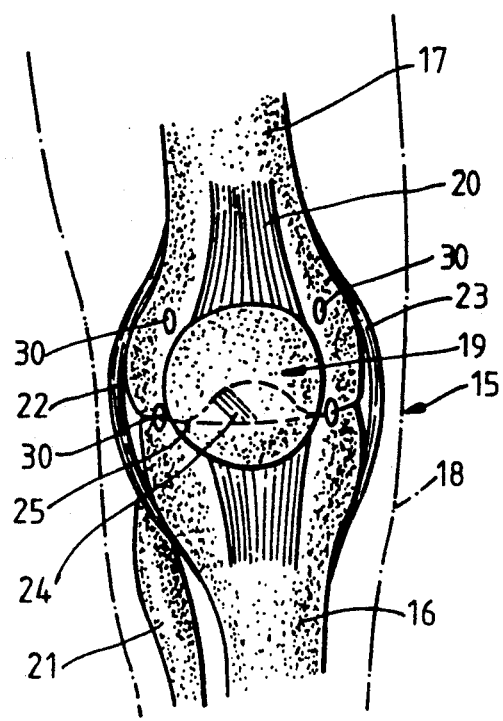
FIG. 1A is a front schematic view of a typical human knee joint.
Figure 1B:
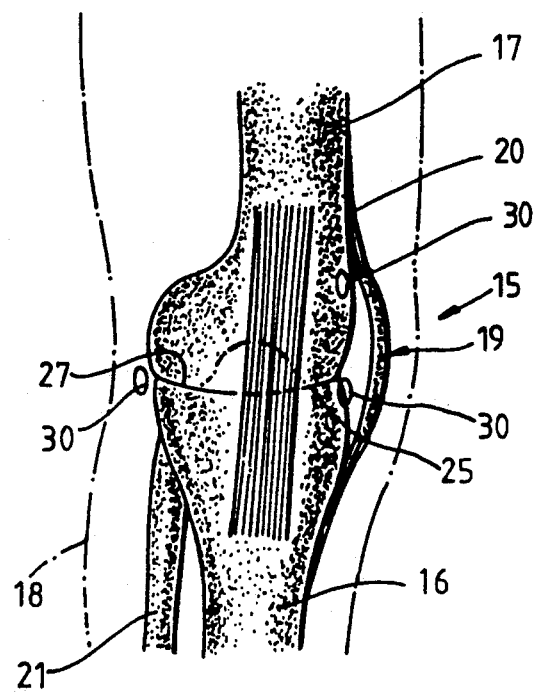
FIG. 1B is a schematic side view of a typical human knee joint.

In FIGS. 1A and 1B, a human knee joint 15 is illustrated, knee joint 15 being representative of one type of joint which may be repaired or replaced by use of the method and apparatus for arthroscopically replacing a bone joint, in accordance with the present invention. Other representative joints for which the present invention may be useful include the elbow, shoulder joint and joints between toes and fingers, hip joint, ankle, and all other joints of the body which can be arthroscopically approached.

Still with reference to FIGS. 1A and 1B, knee joint 15 generally comprises two bones, 16, 17; bone 16 being the tibia, or large lower leg bone, and bone 17 being the femur, or thigh bone. A person's leg is indicated in phantom lines at 18. The patella 19, or knee cap, has the quadraceps extensor femoris muscle 20 holding the patella 19 in place in alignment with a groove in the femur 17, whereby the patella 19 slides within the groove in femur 17 as the leg 18 is bent. Knee joint 15 also includes a fibula 21, or smaller leg bone. A natural knee joint 15 includes a lateral collateral ligament 22, a medial collateral ligament 23, anterior cruciate ligament 24, lateral meniscus 25, and medial meniscus 26. Knee joint 15 has two layers of cartilage. Articular cartilage 27 covers the bone ends of bones 16, 17 or tibia 16 and femur 17. The other cartilage is the menisci, or lateral meniscus 25 and medial meniscus 26. The menisci 25, 26 are thick pads of cartilage that form a rim inside the knee joint 15 and help absorb shock and stabilize the knee joint 15. Damage or disease to the various components of knee joint 15 may sometimes be alleviated through conventional arthroscopic surgery, such as arthroscopic meniscus surgery, arthroscopic surface cartilage surgery, or arthroscopic patella surgery. For such conventional arthroscopic surgery, a plurality of arthroscopic portals 30, or incisions, are made adjacent to knee joint 15 to provide access to knee joint 15 by a conventional arthroscope (not shown), or through which arthroscopic surgical instruments (not shown) may be inserted into knee joint 15. As previously discussed, some damage and disease within a joint, such as knee joint 15, requires more than a repair by conventional arthroscopic surgery, and instead requires a replacement of the joint. The present invention permits knee joint 15 to be replaced by use of the conventional arthroscopic portals, or openings, 30 without the necessity of making major incisions upon leg 18 to expose knee joint 15. It should be noted that conventional arthroscopic portals 30 have a size which is preferably one centimeter in diameter, but arthroscopic openings, or portals, 30 could have a size range from one-half to one and one-half centimeters in diameter.

Figure 2:
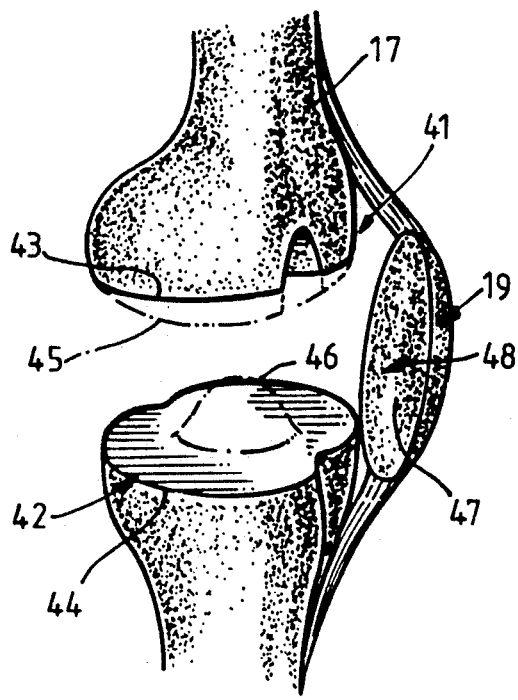
FIG. 2 is an exploded side view of the knee joint of FIG. 1A, illustrating the preparation of the joint for repair in accordance with the present invention.

With reference now to FIGS. 2 and 10, the lower end 41 of femur 17 and the upper end 42 of tibia 16 are shown to illustrate how bones 16 and 17 are prepared for use with the joint surface members (not shown) of the present invention, as will be hereinafter described in greater detail. It is first necessary to remove portions of the upper end 42 of tibia 16 and lower end 41 of femur 17 to arthroscopically form at least one planar surface 43,44 on each bone 16,17 with at least one of the planar surface 43,44 of each bone being disposed opposite each other in a spaced relationship, as illustrated in FIGS. 2 and 10. The original configuration of tibia 16 and femur 17 are illustrated in phantom lines 45,46 and those portions 46 of tibia 16 and 45 of femur 17 are arthroscopically removed, as by use of arthroscopic burrs, drills, cutters or rasps (not shown), which are used along with arthroscopic rulers and depth guides (not shown) to form the desired planar surfaces 43,44. Preferably, the at least one planar surface 43, 44, on each bone 16,17 are disposed parallel to each other when the longitudinal axes of tibia 16 and femur 17 are disposed parallel to each other as illustrated in FIGS. 2 and 10, whereby the cuts, or shaping, of the lower end 41 femur 17 and upper end 42 of tibia 16 are made parallel with each other. If necessary, a planar surface 47 may be formed on the back 48 of patella 19. As will be hereinafter described in greater detail, lower end 41 of femur 17 may be provided with additional planar surfaces, such as planar surfaces 49-52, as illustrated in FIG. 10. It should be noted that all of the shaping, or preparation of, lower end 41 of femur 17 and upper end 42 of tibia 16 is accomplished by use of arthroscopic techniques, requiring only the formation of arthroscopic portals 30 being made adjacent joint 15.

Figure 3:
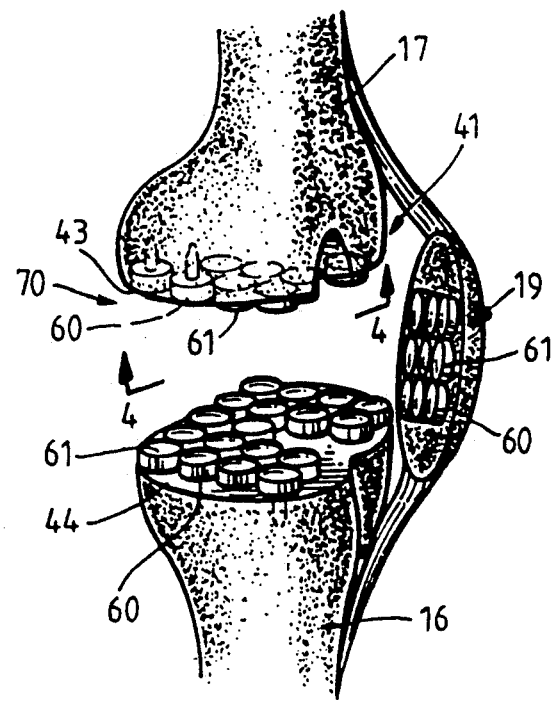
FIG. 3 is an exploded side view of a knee joint replaced in accordance with the present invention.

After bones 16 and 17 have planar surfaces 43 and 44 formed thereon, as previously described, a plurality of joint surface members 60 may be inserted into at least some of the arthroscopic portals 30, and attached to bone planar surfaces 43, 44, as illustrated in FIGS. 3 and 4. As seen in FIGS. 3-5, each joint surface member 60 preferably includes an upper bearing surface 61 formed of a bio-compatible, low friction material and a lower surface 62. Each joint surface member 60 also preferably includes a means for attaching 63 a plurality of joint surface members 60 to a bone planar surface 43, 44; the attachment means 63 being associated with a lower surface 62 of each joint surface member 60. The bio-compatible, low friction material can be any suitable material having the requisite biological compatibility qualities necessary for any prosthetic device implanted within the human body, as well as possess the requisite strength and durability qualities necessary for components used to replace a human joint. The upper bearing surface 61 may be a polished metal surface made from alloys of titanium, aluminum, vanadium, or stainless steel as examples. Alternatively, suitable plastic materials could be utilized, such as TEFLON or a high-molecular weight polyethylene, combinations of metal and plastics, ceramics, or composite materials, such as carbon fiber reinforced materials. As illustrated in FIG. 5, upper bearing surface 61 may be formed integral with each joint surface member 60. Alternatively, upper bearing surface 61 of each joint surface member 60 may be a cap member 65 which is fixedly secured to the joint surface member 60 as illustrated in FIG. 6. cap member 60 may be snapped upon the top portion 66 of joint surface member 60 and held in place by an outwardly extending flange member 67. Alternatively, cap member 65 may be molded upon the top portion 66 of joint surface member 60 and also fixedly secured thereto as by its engagement with flange member 67.

As illustrated in FIGS. 3-6, the cross-sectional configuration of some of the joint surface members 60 may be circular with a diameter, D. Alternatively, as illustrated in FIGS. 7, 8A and 8B, the cross-sectional configuration of some of the joint surface members may be triangular, rectangular or hexagonal. As will be hereinafter described in greater detail, a plurality of joint surface members 60 having any of the foregoing cross-sectional configurations or combinations thereof, are attached to a bone planar surface 43, 44 to cover a substantial portion of each bone planar surface 43, 44 to form the desired replacement joint 70 between bones 16, 17 (FIG. 3). As illustrated in FIG. 3, the upper bearing surfaces 61 of the joint surface members 60 may be a flat, planar surface. Alternatively, as illustrated in FIG. 5, the upper bearing surface 61 of the joint surface members 60 attached to one bone may have a concave configuration 71 (FIGS. 5 and 6), and the upper bearing surface 61 of the joint surface members 60 attached to another bone may have a convex configuration 72, whereby opposing upper bearing surfaces 61 are matingly received within one another.

With reference to FIG. 5, attachment means 63 may be a screw 73, or a pin, nail or staple member 74 having the same general configuration as screw 73; and attachment means 63 is received within a bone planar surface 43, 44, and/or 47 and remains fixedly secured therein. Alternatively, attachment means 63 may be a conventional bio-compatible glue or bone cement 75 disposed on the lower surface 62 of each joint surface member 60, as shown in FIG. 5, in which case screw 73, or pin, nail or staple member 74 would not be utilized. Alternatively, the conventional bio-compatible glue or bone cement 75 could be used on the lower surface 62 of each joint surface member 60 in combination with screw 73 or pin, nail or staple member 74 to further insure the secure attachment of bone joint and/or surface member 60 to bone planar surfaces 43, 44, 47. Additionally, attachment means 63 could include a porous coated surface, such as titanium fiber pads 75, into which the bone 16, 17 may grow. Porous coated surface 75 may preferably be disposed on the lower surface 62 of each joint surface member 60 shown in FIG. 5, if desired. Porous coated surface 75 could also be used in combination with any of the other previously described attachment means 63.

With reference to FIGS. 4-8, it is seen that each joint surface member 60 has three external dimensions including height H, width W, length L. In order for each of the joint surface members 60 to be inserted through the arthroscopic portals 30, at least two of the external dimensions H, W and L of each joint surface member 60 is equal to, or less than, one centimeter. Thus, if the diameter of joint surface member 60 of FIG. 6 is one centimeter, its height and width will each be equal to, or less than, one centimeter, and will be capable of being inserted through arthroscopic portals 30, even if its length exceeds one centimeter. After joint surface member 60 has been inserted through arthroscopic portal 30, it may then be manipulated by an arthroscopic tool and rotated to permit attachment means 63 to be secured into bone planar surface 43, 44.

As illustrated in FIGS. 3, 4, and 7, it is intended that a substantial portion of each bone planar surface 43, 44 and 47, if necessary, shall be covered with joint surface members 60, whereby replacement joint 70 disposed between the two bones, 16, 17 is formed by the upper bearing surfaces 61 of the joint surface members 60, the upper bearing surfaces 61 abutting oppositely disposed upper bearing surfaces 61 as one bone 16 moves with respect to the other bone 17. All of the other joint surface pieces 60 may have the same cross-sectional configuration to form a mosaic pattern upon bone planar surfaces 43, 44, as illustrated in FIGS. 3, 4 and 7; or alternatively, joint surface members 60 having different cross-sectional configurations, such as those illustrated in FIGS. 4, 7, 8A and 8B, may be combined, so as to best cover a substantial portion of each bone planar surface 43, 44 and/or 47. It should be noted that as illustrated in FIGS. 4 and 7, the medullary canal 80 is preferably not covered by joint surface members 60.

With reference to FIG. 9, a method for making mating upper bearing surfaces 61 for joint surface members 60 is illustrated. If desired to have the upper bearing surfaces 61 of the joint surface members 60 attached to the tibia 16 have a concave configuration 71, as previously described in connection with FIG. 5, it may also be desirable to have all of the upper bearing surfaces 61 of joint surface members 60 formed from an integral block of bearing surface material 90 which has a flat, planar lower surface 91 and an upper surface 92 having a concave configuration 93 as illustrated, or on convex configuration. By selecting a block of material 90 which substantially corresponds in size to the planar surface 44 of bone 16, it is then possible to form the plurality of upper bearing surfaces 61 for joint surface members 60 from the block of material 90 as by cutting or sawing the joint surface member 60 from the block of material 90. By then attaching joint surface members 60 upon planar surface member 44 in the same location and angular orientation that each joint member 60 originally had in block of material 90, a substantially continuous concave surface 71 will be formed above bone planar surface 44 by the plurality of bone joint members 60. If a similar block of material having an upper convex surface is utilized to make the joint surface members 60 to be attached to the bone planar surface 43 of bone 17, the convex surface of the other block of material closely conforming to the concave surface 71 of the other block of bearing surface material 90, a substantially continuous convex surface will be formed upon bone planar surface 43 of bone 17, whereby the oppositely disposed upper bearing surfaces 61 of joint surface members 60 having a concave configuration will matingly receive the upper bearing surfaces 61 of joint surface members 60 having a convex configuration so as to form the desired replacement joint 70 between the two bones 16, 17.

With reference to FIGS. 11-13, attachment means 63 may include a plurality of scaffold members, or supporting framework members, 100 upon which are disposed the plurality of joint surface members 60; the scaffold member 100 having upper and lower surfaces 101, 102, the lower surface 62 of each joint surface member 60 being disposed upon an upper surface 101 of one of the scaffold members 100, and the lower surface 102 of each scaffold member 100 is attached to a bone planar surface 43, 44. Scaffold members 100 may be utilized to strengthen the bone 16, 17 and to provide a stronger and more rigid surface upon which to attach the joint surface members 60. Scaffold members 100 can be attached to bone planar surfaces 43, 44 in any manner previously described in connection with attaching a joint surface member 60 to planar surfaces 43, 44, as by: use of screws 73; pin, nail or staple members 74, (staple member 104 being illustrated in FIG. 11, and nail members 105 being illustrated in FIG. 13); a bio-compatible glue or bone cement; a porous coating, all as previously described. The screw, pin, nail or staple members 73, 74, 104, 105, may be secured to the lower surface 102 of each scaffold member 100, or such members may be secured to the lower surface 62 of each joint surface member 60 and then passed through scaffold members 100 as illustrated in FIG. 11.

As with joint surface members 60, each scaffold member 100 has three external dimensions, including height, width, and length as illustrated in FIG. 13. At least two of the three external dimensions H, W, L of each scaffold member 100 is equal to, or less than, one centimeter, in order to permit the insertion of scaffold members 100 through arthroscopic portals 30, as previously described. Dependent upon the dimensions of scaffold members 100, joint surface members 60 may be already attached to scaffold members 100, before they are inserted through arthroscopic portals 30; or alternatively, joint surface member 60 may be attached to scaffold members 100 after scaffold members 100 are already attached to bone planar surfaces 43, 44. Preferably, scaffold members 100 have a height H of approximately six millimeters, and can fall within a range of between four and ten millimeters. Preferably, the width W of each scaffold member 100 is approximately five millimeters, with a range of from three to ten millimeters. Preferably, two to five scaffold members 100 would be used for each bone planar surface, 43, 44, if the joint being replaced were a large joint such as a knee joint 15. For smaller joints, a single scaffold member 100 could be utilized. For example, if the height H of scaffold member 100 is six millimeters thick, a joint surface member 60 could be attached to the upper surface 101 of scaffold member 100 having a distance between its upper bearing surface 61 and lower surface 67 of approximately four millimeters, whereby scaffold member 100 with joint surface member 60 attached thereto, could be initially inserted through a one centimeter wide arthroscopic portal 30. Scaffold members 100 may be provided with an opening 130 (FIG. 13) at their ends to permit them to be manipulated and moved by a suitable arthroscopic tool (not shown).

Still with reference to FIGS. 11-13, scaffold members 100 can be manufactured from any of the materials previously describe in connection with the manufacture of joint surface members 60. Alternatively, joint surface members 60 could comprise the scaffold members 100, and the upper bearing surface 61 of each joint surface member, or scaffold member 100, is formed as an integral part of the upper surface 101 of each scaffold member 100 as will hereinafter be discussed in greater detail in connection with FIGS. 15-18. If scaffold members 100 are utilized as an integral joint surface member 60, with the upper bearing surface 61 formed integral with scaffold member 100, the height H of each scaffold member 100 would be increased to provide the requisite strength characteristics to permit scaffold members 100 to cooperate with a mating scaffold member 100 to serve as the replacement joint 70. As illustrated in FIG. 13, the scaffold members 100 disposed upon bone planar surface 44 of tibia 16 are integral elongate members 110, and such members 110 could be utilized upon planar surface 43 of femur 17. Preferably, scaffold members 100 for femur 17 include additional elongate members 111-114, whereby the scaffold member 100' for femur 17 has a generally J, C, or U-shaped configuration which conforms to the shape of the planar surfaces 43,49-52 formed on femur 17 as previously described in connection with FIG. 10.

Figure 14A:
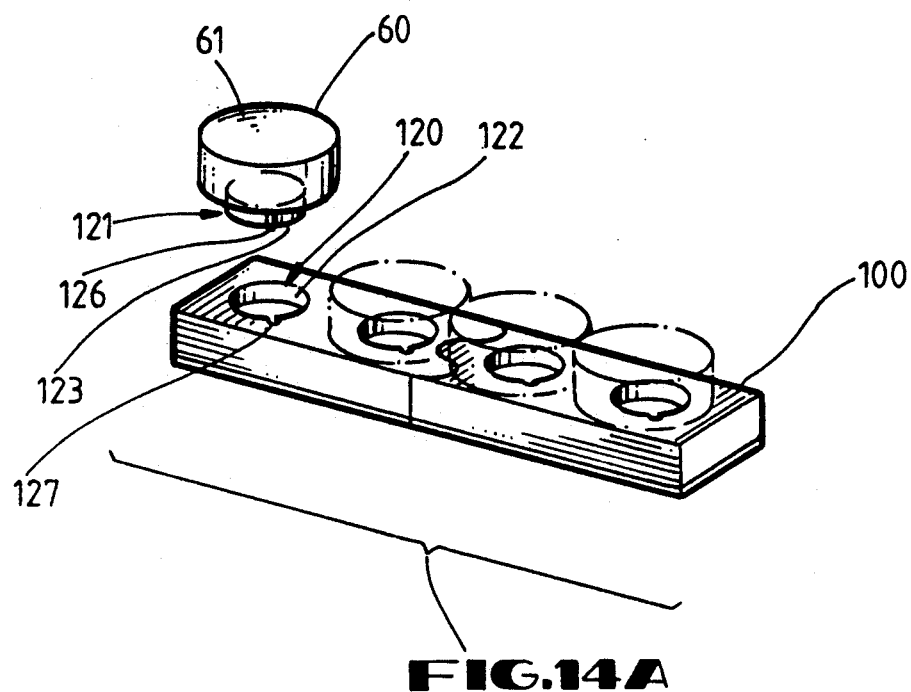
FIGS. 14A and 14B are exploded, perspective views of two embodiments of scaffold members in accordance with the present invention.
Figure 14B:
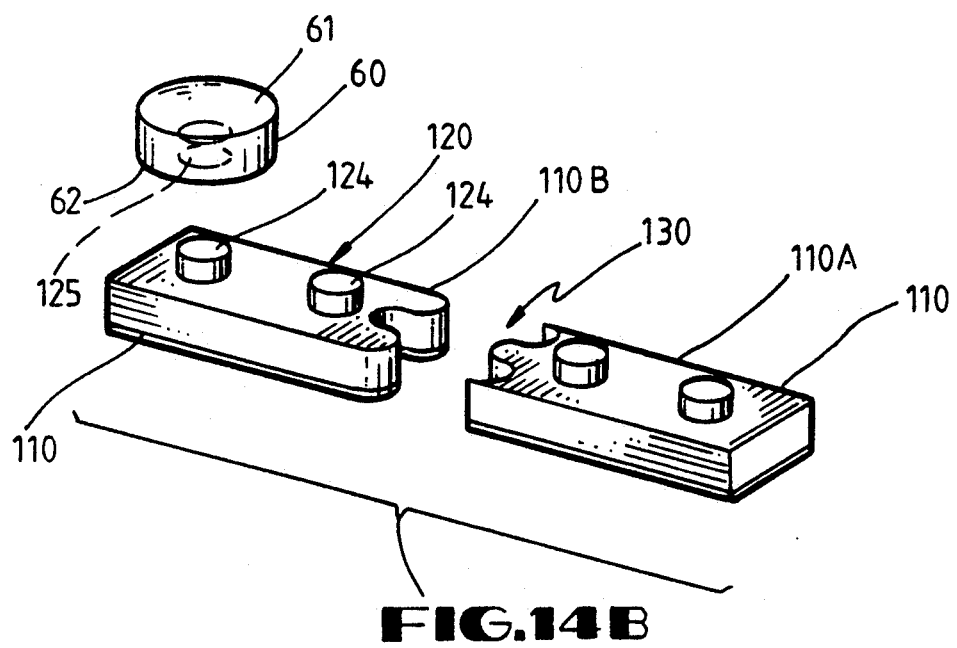

As illustrated in FIGS. 14A, 14B, scaffold members 100, 100', may include a positioning means 120 which cooperates with a mating surface 121 on each joint surface member 60. In the embodiment illustrated in FIG. 14A, positioning means 120 may comprise a circular opening 122 formed in the upper surface 101 of scaffold member 100, with opening 122 receives a correspondingly sized locating pin 123. Locating pin 123 could also have a key 126 which mates with a key shaped opening 127 in opening 122, to properly orientate joint surface member 80 on scaffold 100. In the embodiment illustrated in FIG. 14B, positioning means 120 may comprise a locating pin 124 which mates with a correspondingly sized opening 125 formed in the lower surface 62 of joint surface member 60. Also, as illustrated in FIGS. 14A, 14B, scaffold members 100 can be formed as elongate members 110 formed of connected segments 110A, 110B, including means for connecting 130 the scaffold member segments 110A, 110B. Connecting means 130 can be any suitable connection means, such as illustrated in FIG. 14B or a mating dove tail connection, or any other suitable interlocking connection.

It should be noted that the joint surface members 60 disposed upon scaffold members 100 on bone surface 44 in FIG. 13, and the joint surface members 60 disposed upon the scaffold members 100 on bone planar surface 43 may be formed as previously described in connection with FIG. 9, whereby a substantially, continuous bearing surface is formed by the plurality of joint surface members 60 on tibia 16, which mate with the plurality of joint surface members 60 on femur 17.

With referenced to FIGS. 15-18, joint surface members 60 are shown to be comprised of scaffold members 100, wherein the upper bearing surface 61 of each joint surface member 200, or scaffold 100, is formed as integral part of the upper surface 101 of each scaffold 100. The height H of each scaffold number 100, or joint surface member 200, has been increased to be equal to or less than one centimeter to provide the requisite strength characteristics to permit joint surface members 200 disposed upon femur 17 to cooperate with mating joint surface members 200 disposed upon tibia 16, to serve as the replacement joint 70.

The joint surface members 200 for femur 17 may have a generally C, U, or J-shaped configuration as previously described in connection with the scaffold members 100 of FIGS. 11 and 13. The planar surfaces 43, 44 on femur 17 and tibia 16 are formed as previously described in connection with FIG. 10, and the height H and width W of joint surface members 200 are equal to, or less than one centimeter in length, whereby joint surface members 200 may be passed through the arthroscopic portal 30, as previously described The particular type of replacement joint 70 being formed determines the number of joint surface members 200 to be utilized. In FIG. 15, three joint surface members 200 are illustrated for tibia 16 and femur 17, it being understood that at least two joint surface members 200 would be utilized for forming a replacement joint 70 for a knee joint of an adult. More joint surface members 200 could be utilized if desired. The only limitation on the size of the joint surface members 200 is that two of its three dimensions, H,W, or L, must be equal to, or less than, one centimeter.

Whereas FIG. 15 illustrates the joint surface members 200 being configured to substantially cover a major portion of the planar surface 44 of tibia 16, the joint surface members 200 illustrated in FIGS. 16-18 are shaped to match the outer periphery 210 of the planar surface 44 formed on tibia 16, whereby substantially all of planar surface 44 of tibia 16 is covered by the joint surface members 200, as illustrated in FIG. 18. The joint surface members 200 in the foreground of FIGS. 16 and 17 are shaped to conform to the outer periphery 210 of planar surface 44 on tibia 16; the joint surface members 200 in the background of FIGS. 16 and 17 having the configuration of joint surface members 200 illustrated in FIG. 15. It should be noted that six joint surface members are illustrated in FIG. 16, with the joint surface members 200 abutting against each other along a planar side surface 211 of adjacent joint surface members 200. In FIG. 17, joint surface members 200 are connected by a joint surface member 220 which has a configuration which interlocks with a mating portion 212 of side surfaces 211 of joint surface members 200. The joint surface members 200 of FIG. 18 have an undulating configuration for the side surfaces 211 of joint surface members 200, which undulating side surfaces 211 mate with those of adjacent joint surface members 200.

As previously discussed, it is preferred that the lower surface 215 of each joint surface member 200 be planar to conform to the planar surfaces 43, 44 formed on femur 17 and tibia 16. Preferably, the upper bearing surface 61 of joint surface members 200 for femur 17 have a convex configuration as illustrated in FIG. 15, and the upper bearing surfaces 61 of joint surface members 200 disposed upon tibia 16 have a concave surface 71 as previously described. Joint surface members 200 for tibia 16 could be manufactured as previously described in connection with joint surface members 60 of FIG. 9, in that joint surface members 200 could be formed from an integral block of bearing surface material 90, having a concave surface 71, and the individual joint surface members 200 are formed from the block of bearing surface material 90. Joint surface members 200 may be attached to femur 17 and tibia 16 in any manner previously described, using any of the attachment means 63 previously described.

Figure 19:
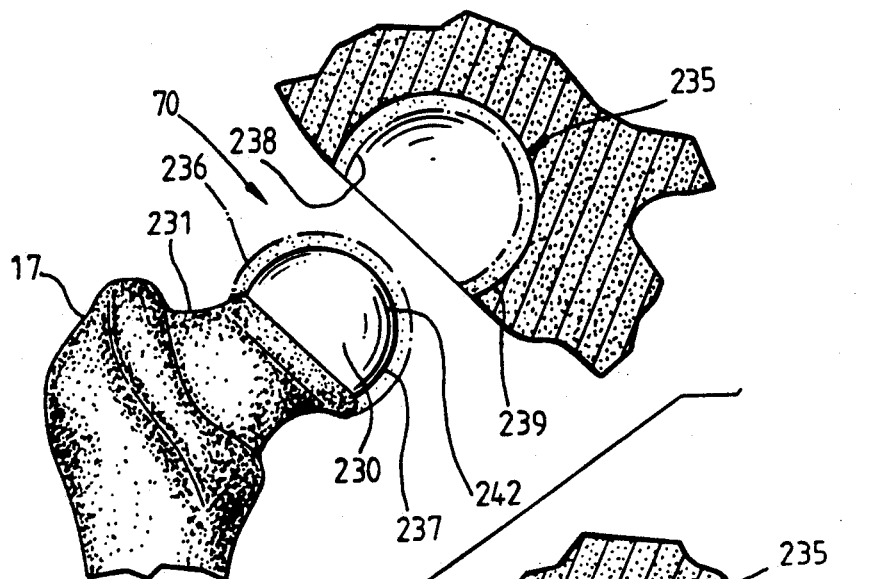
FIG. 19 is a side view illustrating the neck and head of a femur in a spaces relationship from a acetabulum, in which the head of the femur articulates, the femur head and acetabulum being prepared for use in the present invention.
Figure 20:
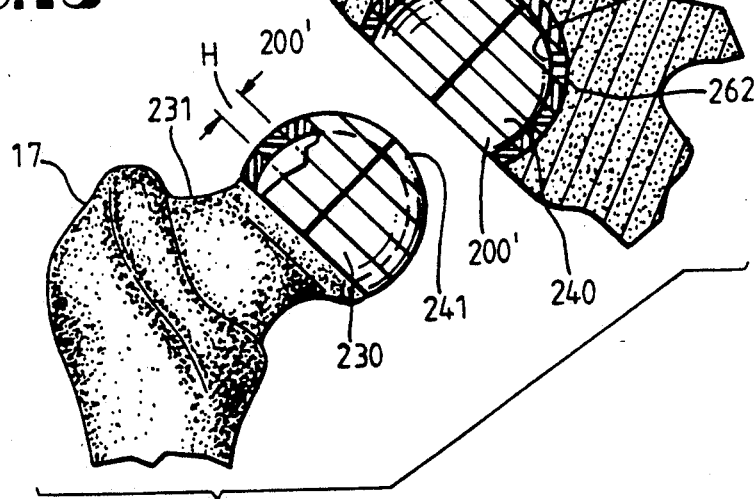
FIG. 20 is a side view of a femur head and acetabulum being provided with the apparatus of the present invention.
Figure 21:
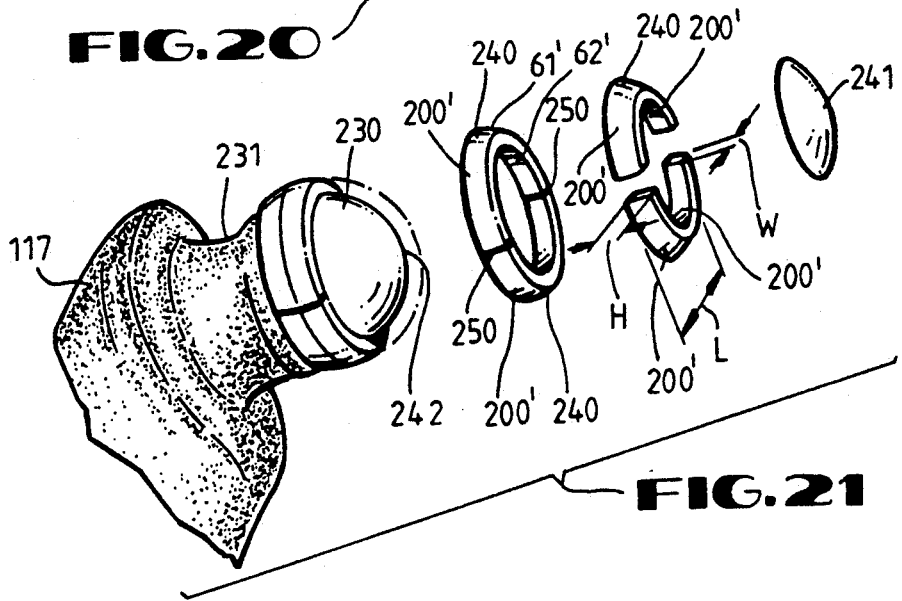
FIG. 21 is an exploded perspective view illustrating a femur head being provided with one embodiment of the apparatus of the present invention.

With reference to FIGS. 19-21, joint surface members 200' are illustrated to form a replacement joint 70' between a femur head 230 disposed upon femur neck 231 on the upper end of femur 17 and an acetabulum 235. As illustrated in FIG. 19, hip joint 70' is prepared for use with joint surface members 200' in a manner similar to that previously described in connection FIG. 10. An outer surface portion 236 of femur head 230 is arthroscopically removed to form a spherical surface 237 on femur head 230. A portion 238 of acetabulum 235 is likewise removed to form a spherical shaped cavity 239. Portions 236, 238 of femur head 230 and acetabulum 235 are arthroscopically removed, as by use of arthroscopic burrs, drills, cutters, or rasps (not shown), which are used along with arthroscopic rulers and depth guides (not shown) to form the desired spherical-shaped surface 237 on femur head 230 and spherical shaped cavity 239 within acetabulum 235. After femur head 230 and acetabulum 235 have been arthroscopically prepared, joint surface members 200' are arthroscopically attached to femur head 230 and acetabulum 235.

Joint surface members 200' may be formed of any of the same materials previously described in connection with joint surface members 60, scaffold members 100, and joint surface members 200, and joint surface members 200' can be attached to surfaces 237, 239 by use of any of the attachment means 63 previously described. Preferably joint surface members 200' for femur head 230 each comprise an elongate member 240 having a generally semi-circular configuration, as illustrated in FIG. 21. Each elongate member 240 as in upper bearing surface 61' which is shaped to closely conform to the bearing surface 261 of the joint surface members 200' of acetabulum 235 as will be hereinafter described in greater detail. The lower surface 62 of each elongate member 240 which forms joint surface member 200' for femur head 230 is shaped to conform to the spherical surface 237 formed on femur head 230. An end cap piece 241 is also provided to cover the end most portion 242 of femur head 230. Joint surface members 200' for acetabulum 235 are likewise formed of a plurality of elongate members 240 which have an outer bearing surface 261 which closely conforms to the outer bearing surface 61' of joint surface members 200' for femur head 230 after femur head 230 in disposed within acetabulum 235. The joint surface members 200' or acetabulum 235 are likewise preferably formed to have a generally semi-circular configuration, the lower surface 262 of the joint surface members 200' for acetabulum 235 being shaped to conform to the spherically shaped cavity surface 239 of acetabulum 235.

By arthroscopically disposing two joint surface members 200' in an abutting relationship as shown at 250 in FIG. 21, the two generally semi-circular configured elongate members 240 form a ring-like member. By succesively, arthroscopically disposing joint surface members 200' upon femur head 230, substantially all of spherical surface 237 of femur head 230 is covered by joint surface members 200', so as to form the femur head portion of replacement hip joint 70'. Likewise, by attaching a plurality of joint surface members 200' within acetabulum 235, the acetabulum 235 is substantially covered by joint surface members 200' to form the acetabulum portion of hip replacement joint 70'. After hip replacement joint 70' has been formed, femur head 230 is urged into acetabulum 235, so that femur head 230, with joint surface members 200' disposed thereon, articulates within acetabulum 235, having joint surface members 200' disposed thereon.

It should be readily apparent to one of ordinary skill in the art that more than two elongate members 240 could be utilized to form the ring-like structure of two abutting joint surface members 200'. For example, four joint surface members 200' are utilized to form one of the ring-like structures in FIG. 21. It should be noted that in order for joint surface members 200' to be arthroscopically disposed upon femur head 230 and within acetabulum 235, as previously described, the height H and width W of elongate members 240 which form joint surface members 200' must be equal to or less than one centimeter, so that joint surface members 200' may be passed through an arthroscopic portal 30, as previously described.

It is to be understood that the invention is not limited to the exact details of construction, operation, exact materials, or embodiments shown and described, as obvious modifications and equivalents will be apparent to one skilled in the art; for example, other cross-sectional configurations of the upper bearing surfaces could be utilized. Accordingly, the invention is therefore to be limited only by the scope of the appended claims.

What is claimed is:

1. An apparatus for arthroscopically replacing a joint between two bones, each bone having at least one prepared surface formed thereon, at least one of the prepared surfaces of each bone being disposed opposite each other in a spaced relationship, comprising:
 a plurality of joint surface members, each joint surface member including an upper bearing surface formed of a bio-compatible, low friction material, and a lower surface;
 a second plurality of joint surface members, each joint surface member including an upper bearing surface formed of a bio-compatible, low friction material, and a lower surface;
 the upper bearing surfaces of the first plurality of joint surface members adapted to be attached to one bone having a concave configuration, and the upper bearing surfaces of the second plurality of joint surface members adapted to be attached to the oppositely disposed bone having a convex configuration, whereby opposing upper bearing surfaces are matingly received within one another;
 first means for attaching the first plurality of joint surface members to a prepared bone surface, he first attachment means being located at the lower surface of each joint surface member of the first plurality of joint surface members;
 second means for attaching the second plurality of joint surface members to a prepared bone surface, the second attachment means located at the lower surface of each joint surface member of the second plurality of joint surface members;
 each of the joint surface members of the first and second plurality of joint surface members having three external dimensions including height, width, and length, and at least two of the external dimensions of each joint surface member is equal to, or less than, one centimeter, whereby the joint surface members may be passed through an arthroscopic portal adjacent to the joint and the first plurality of joint surface members may be attached to one prepared bone surface and the second plurality of joint surface members may be attached to an oppositely disposed bone surface to form a replacement joint between the two bones.

2. The apparatus of claim 1, wherein the first and second attachment means are a staple member associated with the lower surface of the joint surface members.

3. The apparatus of claim 1 wherein, the first and second attachment means are bone cement.

4. The apparatus of claim 1, wherein the first and second attachment means include a porous coating into which the bone may grow.

5. The apparatus of claim 1, wherein at least one of the attachment means includes a plurality of scaffold members upon which are disposed the plurality of joint surface members, the scaffold members having an upper and a lower surface, the lower surface of each joint surface member being disposed upon an upper surface of one of the scaffold members, and the lower surface of each scaffold member is adapted to be attached a prepared bone surface.

6. The apparatus of claim 5, wherein each scaffold member has three external dimensions, including height, width and length, and at least two of the three external dimensions of each scaffold member is equal to, or less than, one centimeter.

7. The apparatus of claim 5, wherein the scaffold members include a positioning means which cooperates with a mating surface on each joint surface member.

8. The apparatus of claim 5, wherein the scaffold members are integral elongate members.

9. The apparatus of claim 5, wherein the scaffold members are elongate members formed of connected segments, and include means for connecting the segments of the scaffold members.

10. The apparatus of claim 5, wherein one of the bones is a femur having a plurality of planar thereon and the scaffold members which are adapted for attachment to the planar surfaces of the femur have a U-shaped configuration which conforms to the shape of the prepared surfaces on the femur.

11. The apparatus of claim 5, wherein the upper bearing surface of each joint surface member is formed as an integral part of the upper surface of each scaffold member.

12. The apparatus of claim 1, wherein the upper bearing surface is formed integral with each joint surface member of at least one of the plurality of joint surface members.

13. The apparatus of claim 1, wherein the upper bearing surface of each joint surface member of at least one of the plurality of joint surface members is a cap member fixedly secured to the joint surface member.

14. The apparatus of claim 1, wherein the cross-sectional configuration of some of the joint surface members of at least one of the plurality of joint surface members is circular.

15. The apparatus of claim 1, wherein the cross-sectional configuration of some of the joint surface members of at least one of the plurality of joint surface members is triangular.

16. The apparatus of claim 1, wherein the cross-sectional configuration of some of the joint surface members of at least one of the plurality of joint surface members is rectangular.

17. The apparatus of claim 1, wherein the cross-sectional configuration, of some of the joint surface members of at least one of the plurality of joint surface members is hexagonal.

18. The apparatus of claim 1, wherein the upper bearing surfaces of each joint surface member of at least one of the plurality of joint surface members is planar.

19. The apparatus of claim 1, wherein the joint surface members of at least one of the plurality of joint surface members are elongate members which have a generally semi-circular configuration, and are adapted to be attached to an arthroscopically prepared bone surface on the head of a femur and within an acetabulum.

20. A method for arthroscopically replacing a joint between two bones, comprising the steps of:
    forming a plurality of arthroscopic portals adjacent the joint;
    inserting an arthroscope through one of the arthroscopic portals;
    arthroscopically preparing at least one surface on each bone, with at least one of the prepared surfaces of each bone being disposed opposite each other in a spaced relationship;
    inserting a plurality of joint surface members through at least some of the arthroscopic portals, each joint surface member including an upper bearing surface formed of a bio-compatible, low friction material, and a lower surface;
    attaching the plurality of joint surface members to the prepared bone surfaces to cover a substantial portion of each prepared bone surface, whereby a replacement joint between the two bones is formed by the upper bearing surfaces of the joint surface members, which upper bearing surfaces abut oppositely disposed upper bearing surfaces as one bone moves with respect to the other bone.

21. The method of claim 20, including the step of: inserting a plurality of scaffold members through some of the arthroscopic portals; attaching the scaffold members to the prepared bone surfaces; and attaching the joint surface members to the scaffold members.

22. The method of claim 21, wherein one of the bones is a femur, further including the step of: arthroscopically forming a plurality of planar surfaces on the femur in a J-shaped configuration; attaching a plurality of J, C, or U-shaped scaffold members to the femur planar surfaces; and attaching a plurality of joint surface members to the scaffold members.

23. The method of claim 21, including the steps of utilizing the scaffold members as the joint surface members, and forming the upper bearing surface of the joint surface members as an integral part of an upper surface of each scaffold member.

24. The method of claim 20, including the steps of: forming the upper bearing surfaces from a single block of bearing surface material having a shape approximating the shape of the prepared bone surface to be covered; disposing the upper bearing surfaces upon the prepared bone surface in the same location and orientation the upper bearing surfaces originally had with respect to the block of bearing surface material, whereby the plurality of upper bearing surfaces form a substantially continuous bearing surface on the prepared bone surface.

25. The method of claim 24, including the step of utilizing a block of bearing surface material which has a planar lower surface and either a concave or convex upper surface.

26. The method of claim 23, including the steps of: forming the scaffold members from a single block of bearing surface material having a shape approximating the shape of the prepared bone surface to be covered; disposing the scaffold members upon the prepared bone surface in the same location and orientation the scaffold members originally had with respect to the block of bearing surface material, whereby the upper surfaces of the scaffold members form a substantially continuous bearing surface on the prepared bone surface.

27. The method of claim 20, including the steps of: utilizing a plurality of elongate joint surface members which have a generally semi-circular configuration; arthroscopically attaching a plurality of the joint surface members upon a prepared bone surface on a head of a femur and within an acetabulum to form a replacement hip joint.

28. The apparatus of claim 1, wherein the attachment means is a screw associated with the lower surface of the joint surface members.

29. The apparatus of claim 1, wherein the attachment means is a pin associated with the lower surface of the joint surface members.

30. The apparatus of claim 1, wherein the attachment means is a nail associated with the lower surface of the joint surface members.

31. The apparatus of claim 1, wherein the attachment means is a bio-compatible glue.

32. The apparatus of claim 5, wherein one of the bones is a femur having a plurality of planar bone surfaces thereon and the scaffold members which are adapted for attachment to the planar surfaces of the femur have a J-shaped configuration which conforms to the shape of the prepared surfaces on the femur.

33. The apparatus of claim 5, wherein one of the bones is a femur having a plurality of planar bone surfaces thereon and the scaffold members which are adapted for attachment to the planar surfaces of the femur have a C-shaped configuration which conforms to the shape of the prepared surfaces on the femur.

* * * * *

UNITED STATES PATENT AND TRADEMARK OFFICE
CERTIFICATE OF CORRECTION

PATENT NO.  : 5,263,987
DATED       : November 23, 1993
INVENTOR(S) : Mrugesh K. Shah It is certified that error appears in the above-identified patent and that said Letters Patent is hereby corrected as shown below:

In Claim 1, Column 12, Line 47, delete "he", and insert -- the --.

In Claim 10, Column 13, Line 35, after "planar", insert -- bone surfaces --.

Signed and Sealed this

Twenty-sixth Day of April, 1994

Attest:

BRUCE LEHMAN

*Attesting Officer*      *Commissioner of Patents and Trademarks*